(12) United States Patent
Jordan et al.

(10) Patent No.: US 12,128,252 B2
(45) Date of Patent: Oct. 29, 2024

(54) NO-VIEW INTERFRACTION TREATMENT TARGET MOTION MANAGEMENT USING VOLUMETRIC IMAGING

(71) Applicant: Accuray Incorporated, Sunnyvale, CA (US)

(72) Inventors: Petr Jordan, Redwood City, CA (US); Calvin R. Maurer, Jr., San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 634 days.

(21) Appl. No.: 15/862,461

(22) Filed: Jan. 4, 2018

(65) Prior Publication Data

US 2018/0193669 A1 Jul. 12, 2018

Related U.S. Application Data

(60) Provisional application No. 62/443,583, filed on Jan. 6, 2017.

(51) Int. Cl.
*A61B 5/00* (2006.01)
*A61B 6/00* (2006.01)
(Continued)

(52) U.S. Cl.
CPC ............ *A61N 5/1049* (2013.01); *A61B 6/032* (2013.01); *A61B 6/4258* (2013.01); *A61B 6/486* (2013.01);
(Continued)

(58) Field of Classification Search
CPC .............................. A61N 5/1049; A61N 5/107
See application file for complete search history.

(56) References Cited

U.S. PATENT DOCUMENTS

| 2006/0074292 A1 | 4/2006 | Thomson et al. |
| 2007/0071176 A1 | 3/2007 | Main et al. |

(Continued)

FOREIGN PATENT DOCUMENTS

| CN | 101076282 A | 11/2007 |
| CN | 101268474 A | 9/2008 |

(Continued)

OTHER PUBLICATIONS

Int'l Search Report and Written Opinion of the ISA/EP in PCT/US2018/012660 dated May 2, 2018; 9 pgs.

(Continued)

*Primary Examiner* — Rajeev P Siripurapu
(74) *Attorney, Agent, or Firm* — Womble Bond Dickinson (US) LLP

(57) ABSTRACT

A method of the present disclosure includes identifying, based on a reference image, a full motion range of a target, wherein the full motion range of the target defines a full internal target volume (ITV). The method further includes identifying a non-target object in a motion image or the reference image. The method further includes performing a volumetric alignment of the ITV and the non-target object. The method further includes modifying a non-target to target displacement vector based on the volumetric alignment. The method further includes tracking the target based on the modified non-target to target displacement vector.

16 Claims, 11 Drawing Sheets

(51) Int. Cl.
  *A61B 6/03* (2006.01)
  *A61B 6/42* (2024.01)
  *A61B 6/50* (2024.01)
  *A61N 5/10* (2006.01)

(52) U.S. Cl.
  CPC .............. *A61B 6/50* (2013.01); *A61B 6/5235* (2013.01); *A61N 5/1045* (2013.01); *A61N 5/1067* (2013.01); *A61N 5/1069* (2013.01); *A61N 5/107* (2013.01); *A61N 5/1081* (2013.01); *A61N 5/1083* (2013.01); *A61N 2005/1055* (2013.01); *A61N 2005/1061* (2013.01)

(56) References Cited

U.S. PATENT DOCUMENTS

| | | | |
|---|---|---|---|
| 2008/0130825 A1 | 6/2008 | Fu et al. | |
| 2009/0003523 A1 | 1/2009 | Raanes et al. | |
| 2011/0092793 A1 | 4/2011 | Thomson et al. | |
| 2012/0008735 A1* | 1/2012 | Maurer .................. | A61B 6/025 378/5 |
| 2012/0106704 A1* | 5/2012 | Maurer, Jr. .......... | A61N 5/1077 378/65 |
| 2012/0109608 A1 | 5/2012 | Core et al. | |
| 2012/0230464 A1 | 9/2012 | Ling et al. | |
| 2015/0016586 A1 | 1/2015 | Maurer, Jr. et al. | |
| 2018/0015305 A1 | 1/2018 | Maurer, Jr. et al. | |
| 2021/0106704 A1 | 4/2021 | Schermerhorn et al. | |

FOREIGN PATENT DOCUMENTS

| | | |
|---|---|---|
| CN | 101854848 A | 10/2010 |
| CN | 103099630 A | 5/2013 |
| CN | 103229178 A | 7/2013 |
| CN | 104587609 | 5/2015 |
| IN | 102274039 A | 12/2011 |
| JP | 2008-514352 A | 5/2008 |
| JP | 2013 123528 A | 6/2013 |
| JP | 2013-544137 A | 12/2013 |
| JP | 5812841 B2 | 11/2015 |
| WO | 2012058609 A2 | 5/2012 |
| WO | 2012058615 A1 | 5/2012 |
| WO | 2018129375 A1 | 7/2018 |

OTHER PUBLICATIONS

Notification of First Office Action from the China National Intellectual Property Administration (CNIPA) for Chinese Patent Application No. 201910971664.5, dated Jul. 7, 2021, pp. 11.
Notification of First Office Action from the China National Intellectual Property Administration (CNIPA) for Chinese Patent Application No. 201910971664.5, dated Dec. 16, 2020, pp. 10.
EP Search Report dated Dec. 6, 2019 from related EP Application No. 19192390, filed Aug. 19, 2019, 2 pages.
CN Search Report dated Dec. 11, 2020 from related CN Application No. 201910971664, filed Oct. 14, 2019, 2 pages.
CN Search Report dated Oct. 28, 2022 from related CN Application No. 201880015808, filed Sep. 4, 2019, 2 pages.
JP Office Action—Refusal dated Nov. 9, 2022 from related JP Application No. 2019536824, filed Jan. 5, 2018, 3 pages.
Office Action for European Patent Application No. 19192390.3 mailed on Feb. 12, 2024.

* cited by examiner

NO-VIEW INTERFRACTION TREATMENT TARGET MOTION MANAGEMENT USING VOLUMETRIC IMAGING

PRIORITY CLAIM

This application claims the benefit of U.S. Provisional Application No. 62/443,583 filed on Jan. 6, 2017, the entire contents of which are hereby incorporated by reference.

TECHNICAL FIELD

The present disclosure relates to radiation treatment target motion management.

BACKGROUND

A treatment target may move during image guided treatment such as radiation treatment. To account for such movement, traditional radiation delivery systems treat the Internal Target Volume (ITV), i.e., the entire range of motion of the target during respiration or other movement, with a margin of expansion to compensate for setup inaccuracy, gross patient movement during treatment, and change of breathing pattern or other motion pattern between planning and treatment. This approach, however, comes with the drawback of large volumes of normal tissue being exposed to the prescription dose, especially in cases where the tumor undergoes a large excursion during breathing.

BRIEF DESCRIPTION OF THE DRAWINGS

The present disclosure will be understood more fully from the detailed description given below and from the accompanying drawings of various implementations of the disclosure.

DETAILED DESCRIPTION

Figure 1A:
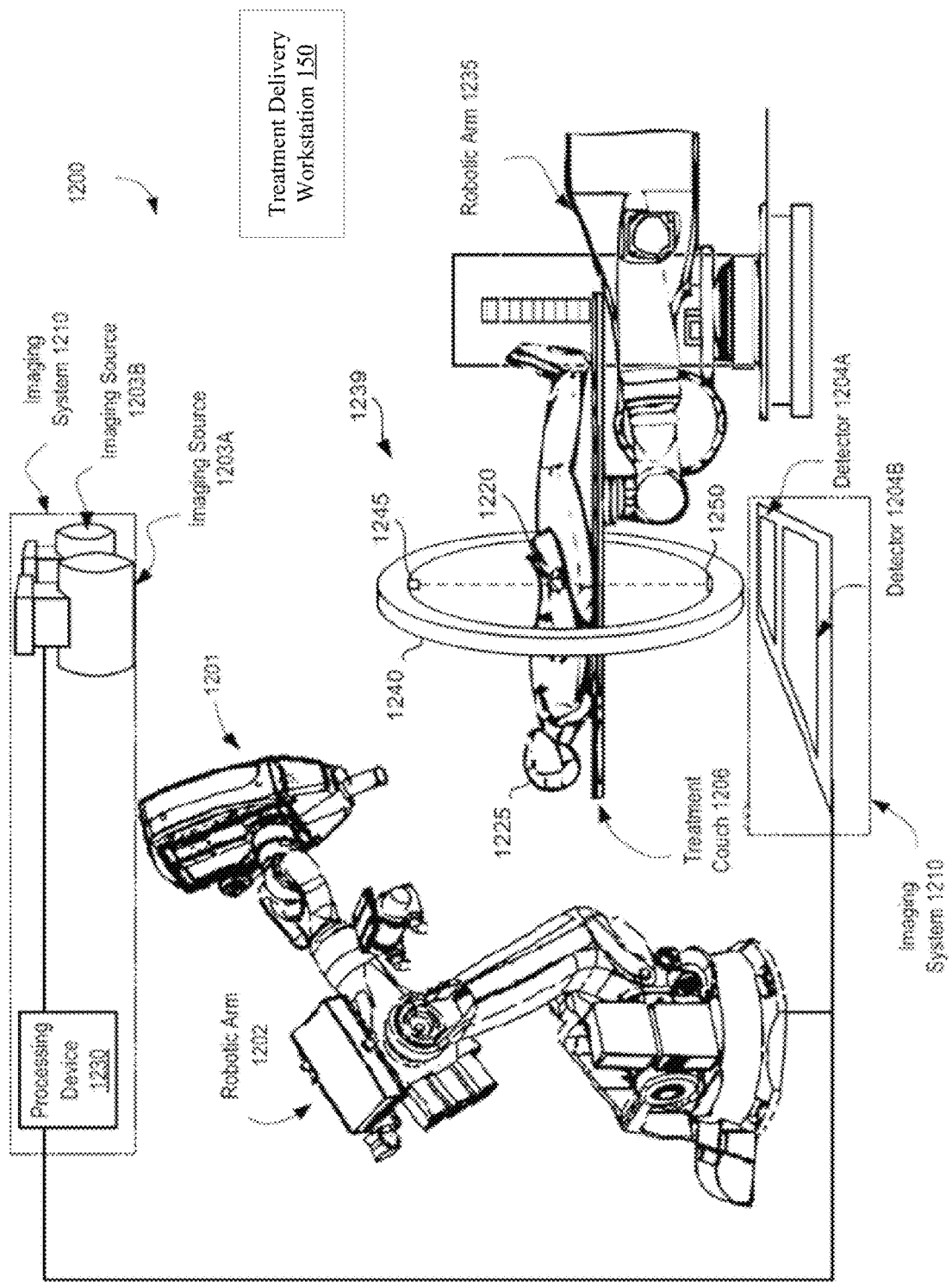
FIG. 1A illustrates a radiation treatment system that may be used in accordance with embodiments described herein.

Described herein are embodiments of methods and apparatus for radiation treatment target motion management. Treatment target motion management is an important aspect of radiation therapy and radiosurgery. In the broadest sense, motion management involves two stages: (1) determination of a target's position and (2) delivery of the treatment beam based on the target's position (e.g., dynamic target tracking, gating, treatment interruption, treatment plan adaptation).

Embodiments of this disclosure are directed to methods for using intrafraction volumetric imaging to significantly reduce motion management uncertainties due to interfraction setup error and interfraction baseline shifts. These types of target position variation are a challenge in lung, pancreas, liver, and other abdominal treatment sites. Embodiments of the present disclosure may be used with a radiation treatment delivery system such as the CyberKnife® radiosurgery system that includes stereo x-ray imaging capability. Alternatively, other types of radiation treatment delivery systems (e.g., gantry based, helical based, etc.) may be used.

In lung application specifically, the CyberKnife® radiosurgery system offers a soft tissue tracking solutions for 2-View, 1-view, and 0-view tracking. 2-View is a tracking method that tracks tumors in the lung directly without the use of fiducials using image intensity differences between the lesion and the background.

1-view is a tracking method that may be used, for example, in conjunction with Accuray's Synchrony® Respiratory Tracking System that continuously synchronizes beam delivery with the motion of the target resulting from respiration, without the need to interrupt the treatment or move the patient. It allows clinicians to significantly reduce margins, while eliminating the need for gating or breath-holding techniques. 1-view tracks tumor motion in one of two X-ray projections allowing accurate dose delivery with radiosurgical margins in the tracked direction. Under this scenario an ITV expansion is applied in the non-tracked X-ray projection.

In one embodiment, for 1-view tracking, a 3D scan is acquired at the beginning of a treatment fraction to perform direct target alignment. This operation effectively removes the interfraction baseline shift. Subsequent target motion (i.e. respiratory motion) is managed via 1-view tracking, in which the target motion within a plane coincident with the patient inferior-superior axis is tracked directly. The orthogonal component of motion is not tracked. Instead, a partial ITV is used based on target motion amplitude estimated from 4D CT (or 3D inhale/exhale CT pair).

0-view tracking is a treatment method that applies in situations when a lung tumor is not clearly visible in either X-ray projection. 0-view uses ITV expansion in two X-ray projections and Xsight Spine Tracking System to track patient position. In one embodiment, of 0-view tracking, the treatment target is not tracked directly. Instead, a proxy structure (e.g., a non-target object), such as the spine of a patient, is tracked by the system to account for gross patient motion, while the motion of the target is managed indirectly.

The target position is estimated using a displacement vector between a reference point on the spine and the center of the target as defined by a planning image. During treatment, the same displacement vector may be applied after each spine tracking correction in order to estimate the position of the target. This approach may compensate for intrafraction gross patient motion. The interfraction baseline shifts, setup error, and intrafraction respiratory motion and baseline shift may be accounted for by an ITV, and a PTV expansion may be used to account for the described sources of uncertainty.

In patients treated with 2-View tracking, the interfraction and intrafraction components of target motion are detected and fully compensated. In 1-view tracking, the inter- and intra-fraction target motions are tracked directly only in one plane orthogonal to the active imager. The third axis motion is "blind," requiring other methods of estimating inter- and intra-fraction components of motion. In one particular embodiment, for example, where a CyberKnife® radiosurgery system is used with Lung Optimized Treatment™ (LOT) tools, the intra-fraction component may be estimated from preoperative 4D CT scan (or in other embodiments, from other scans, such as a pair of inhale/exhale CT scans), while the interfraction motion is managed by a planning target volume (PTV) margin sufficiently large to cover expected variations in the entire patient population. It should be noted that embodiments of the present invention are discussed in relation 0-View, 1-View and 2-View only for ease of discussion and that the methods and systems discussed herein may be used with other tracking methodologies.

The use of a volumetric imaging system (e.g., the medPhoton ImagingRing System (IRS)) with a radiation treatment delivery system (e.g., the CyberKnife® radiation treatment system) as shown in FIG. 1A enables new image registration and image tracking opportunities. Worth noting, the term "tracking" used herein may refer to both tracking a treatment target in the treatment planning stages (e.g., determining a location of the treatment target) as well as tracking the treatment target during treatment (e.g., actively updating a location of the treatment target). While the volumetric imaging system (e.g., 1239) may provide superior anatomical information and robust patient alignment, the stereoscopic x-ray imaging system (e.g., 1210) enables frequent intrafraction imaging and tracking. In an alternative embodiment, a radiation therapy device with an integrated in-room diagnostic computer tomography (CT) may be used. With an in-room diagnostic CT, the patient is physically moved (e.g., using a robotic couch) between an in-room diagnostic scanner and the radiation treatment delivery system.

As used herein, "registration" (also referred to herein as "image registration") of medical images refers to the determination of a mathematical relationship between corresponding anatomical or other features (e.g. fiducials) appearing in those medical images. In one embodiment, patients may be imaged multiple times, either with a single modality, or with different modalities. On step when interpreting and comparing image sets is the establishment of correspondence between different points in the multiple images. Image registration is the process of computing a mapping or transformation between coordinates in one image space and those in another. This transformation results in the same anatomical points in different image sets being mapped to each other, and can be used to fuse image sets in order to use the combined imaging information for diagnosis and treatment.

Image registration and fusion may be useful in a variety of contexts, including when combining complementary structural information such as soft tissue from MR with bone from CT. Image fusion is also very useful for interpreting functional imaging. When functional PET or fMR images are fused with high-resolution anatomical images, the functional properties can be linked to the anatomical structures in which they occur.

Registration can include, but is not limited to, the determination of one or more spatial, alignment or intrafraction transformations that, when applied to one or both of the medical images, would cause an overlay of the corresponding anatomical features. The spatial or alignment or intrafraction transformations can include rigid-body transformations and/or deformable transformations and can, if the medical images are from different coordinate systems or reference frames, account for differences in those coordinate systems or reference frames.

Image registration in general may involve computation of similarity values or, equivalently, difference values (e.g., cross correlation, entropy, mutual information, gradient correlation, pattern intensity, gradient difference, image intensity gradients) that are evaluated to determine a spatial transformation between a target's location in a planning room image and a target's location in a treatment room image. Other methods of image registration may be utilized. For cases in which the medical images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times.

Various image registration methods may be utilized with the embodiments described herein. In one example, pointbased registration may be used. Points are simple geometrical features that can be used for medical image registration. Point-based registration involves determining the 3-D coordinates of corresponding points in the two images and computing the transformation that best aligns these points.

In another embodiment, surface-based registration may be used. The 3-D boundary or surface of an anatomical object or structure is a geometrical feature that can be used for medical image registration. Surface-based image registration methods may involve determining corresponding surfaces in the two images and computing the transformation that best aligns these surfaces. Whereas point-based registration involves aligning a generally small number of corresponding fiducial points, surface-based registration involves aligning a generally much larger number of points for which no point correspondence information is available.

In another embodiment, intensity-based registration may be used. Intensity-based registration may involve calculating a transformation between two images using a measure of alignment based only on the values of the pixels or voxels in the images. In other embodiments, other methods of image registration may be used.

The term alignment transformation (e.g., volumetric alignment) refers herein to a transformation between a first coordinate system (for example and not by way of limitation a planning image coordinate system of a patient) and a second coordinate system (a treatment room coordinate system) whereby the alignment transformation determines the location of a target in the second coordinate system relative to the first coordinate system, for example and not by way of limitation at the time of patient setup prior to commencement of the treatment fraction.

The term intrafraction transformation refers herein to a transformation between the first coordinate system and the second coordinate system whereby the intrafraction transformation determines the location of the target in the first coordinate system relative to the second coordinate system following commencement of the procedure, for example and not by way of limitation during the treatment fraction.

The term target may refer to one or more fiducials near (within some defined proximity to) a treatment area (e.g., a tumor). In another embodiment a target may be a bony structure. In yet another embodiment a target may refer to soft tissue of a patient. A target may be any defined structure or area capable of being identified and tracked, as described herein.

There is a need to improve on image registration methods to increase the accuracy and computational efficiency in locating a target in one or more images, and thereby more accurately and efficiently determine the spatial transformation between the target's location in a treatment room reference frame relative to a treatment planning image reference frame.

FIG. 1A illustrates a radiation treatment system 1200 that may be used in accordance with embodiments described herein. As shown, FIG. 1A illustrates a configuration of a radiation treatment system 1200. In the illustrated embodiments, the radiation treatment system 1200 includes a linear accelerator (LINAC) 1201 that acts as a radiation treatment source. In one embodiment, the LINAC 1201 is mounted on the end of a robotic arm 1235 having multiple (e.g., 5 or more) degrees of freedom in order to position the LINAC 1201 to irradiate a pathological anatomy (e.g., target 120) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 1201 may be mounted on a gantry based system as described below.

LINAC 1201 may be positioned at multiple different nodes (predefined positions at which the LINAC 1201 is stopped and radiation may be delivered) during treatment by moving the robotic arm 1235. At the nodes, the LINAC 1201 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 103A, 1203B and/or x-ray detectors 1204A, 1204B may be mobile, in which case they may be repositioned to maintain alignment with the target 120, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1A, the image-guided radiation treatment system 1200 may further be associated with a treatment delivery workstation 150. The treatment delivery workstation may be remotely located from the radiation treatment system 1200 in a different room that the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

In some embodiments, a gantry system with a helical delivery may be used to rotate the imaging system 1210. For example, the gantry system may be used to acquire two, three, or more images (e.g., x-ray images) at different angles. The radiation treatment delivery system may also include a rotational imaging system 109 that is positioned around the patient.

In one implementation, the system 1200 includes a frameless robotic radiosurgery system (e.g., CyberKnife® treatment delivery system). In another implementation, the system 1200 is coupled to a gantry-based LINAC treatment system where, for example, LINAC 1201 is coupled to a gantry of a gantry based system. Alternatively, system 1200 may be used with other types of radiation treatment systems, for example, a helical delivery system as discussed below.

Figure 1B:
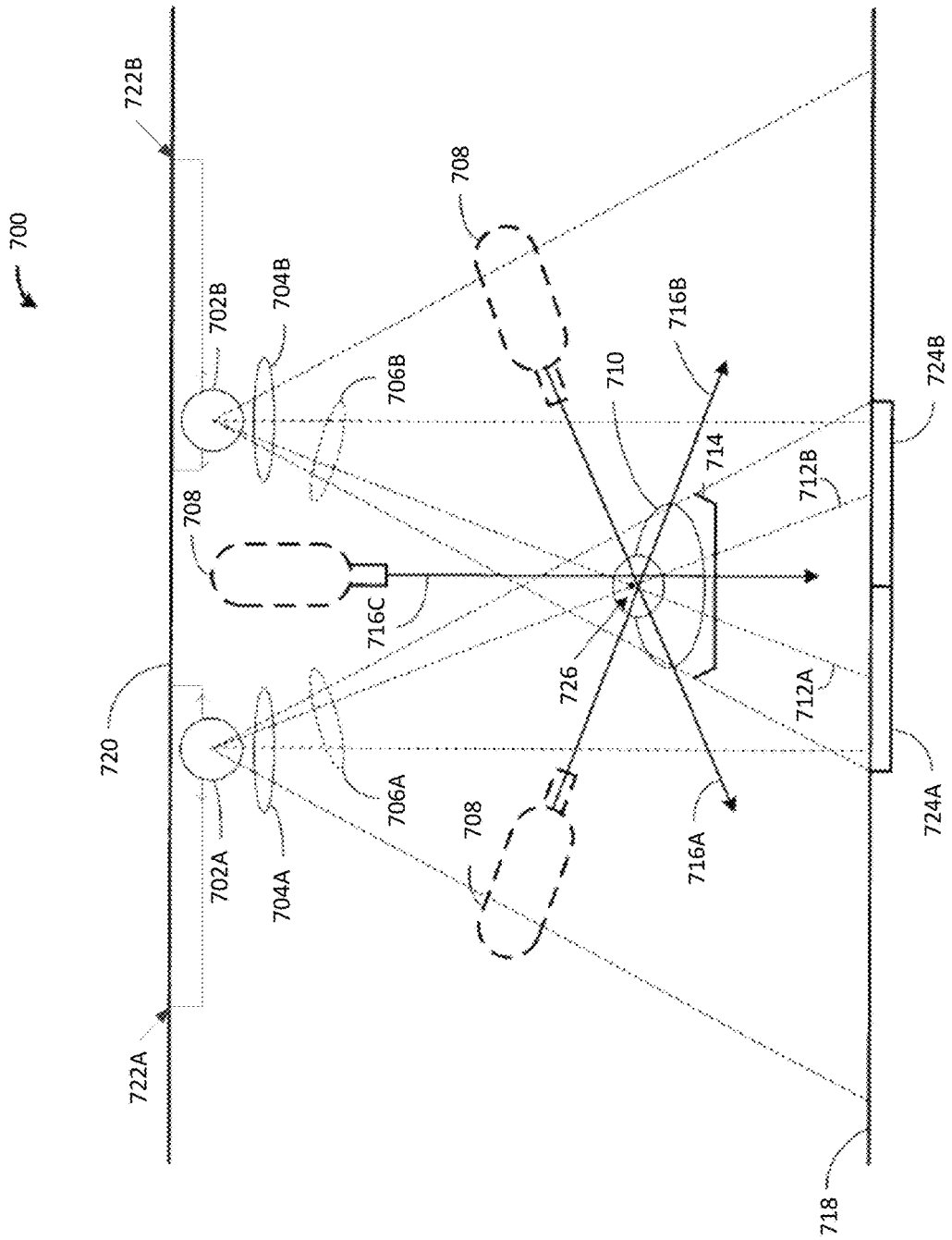
FIG. 1B is a cross-section of the radiation treatment system in accordance with embodiments described herein.

FIG. 1B illustrates the configuration of an image-guided radiation treatment (IGRT) system 700. In general, the IGRT system 700 may correspond to the radiation treatment system 1200 of FIG. 1A.

As shown in FIG. 1B, the IGRT system 700 may include to kilovoltage (kV) imaging sources 702A and 702B that may be mounted on tracks 722A and 722B on the ceiling 720 of an operating room and may be aligned to project imaging x-ray beams 704A and 704B from two different positions such that a ray 712A of beam 704A intersects with a ray 712B of beam 704B at an imaging center 726 (i.e., isocenter), which provides a reference point for positioning the LINAC 708 to generate treatment beams 716A, 716B and 716C and the patient 710 on treatment couch 714 during treatment. After passing through the patient 710, imaging x-ray beams 704A and 704B may illuminate respective imaging surfaces of x-ray detectors 724A and 724B, which may be mounted at or near the floor 718 of the operating room and substantially parallel to each other (e.g., within 5 degrees). The kV imaging sources 702A and 702B may be substantially coplanar such that the imaging surfaces of kV imaging sources 702A and 702B form a single imaging plane. In one embodiment, kV imaging sources 702A and 702B may be replaced with a single kV imaging source. Once an x-ray image of the patient 710 has been generated, the LINAC 708 may rotate to generate a treatment beam 716 from a different angle. While the LINAC 708 rotates to the different angle, the kV imaging sources 702A and 702B may move along tracks 722A and 722B to generate x-ray images of the patient 710 from a new angle.

Figure 2A:
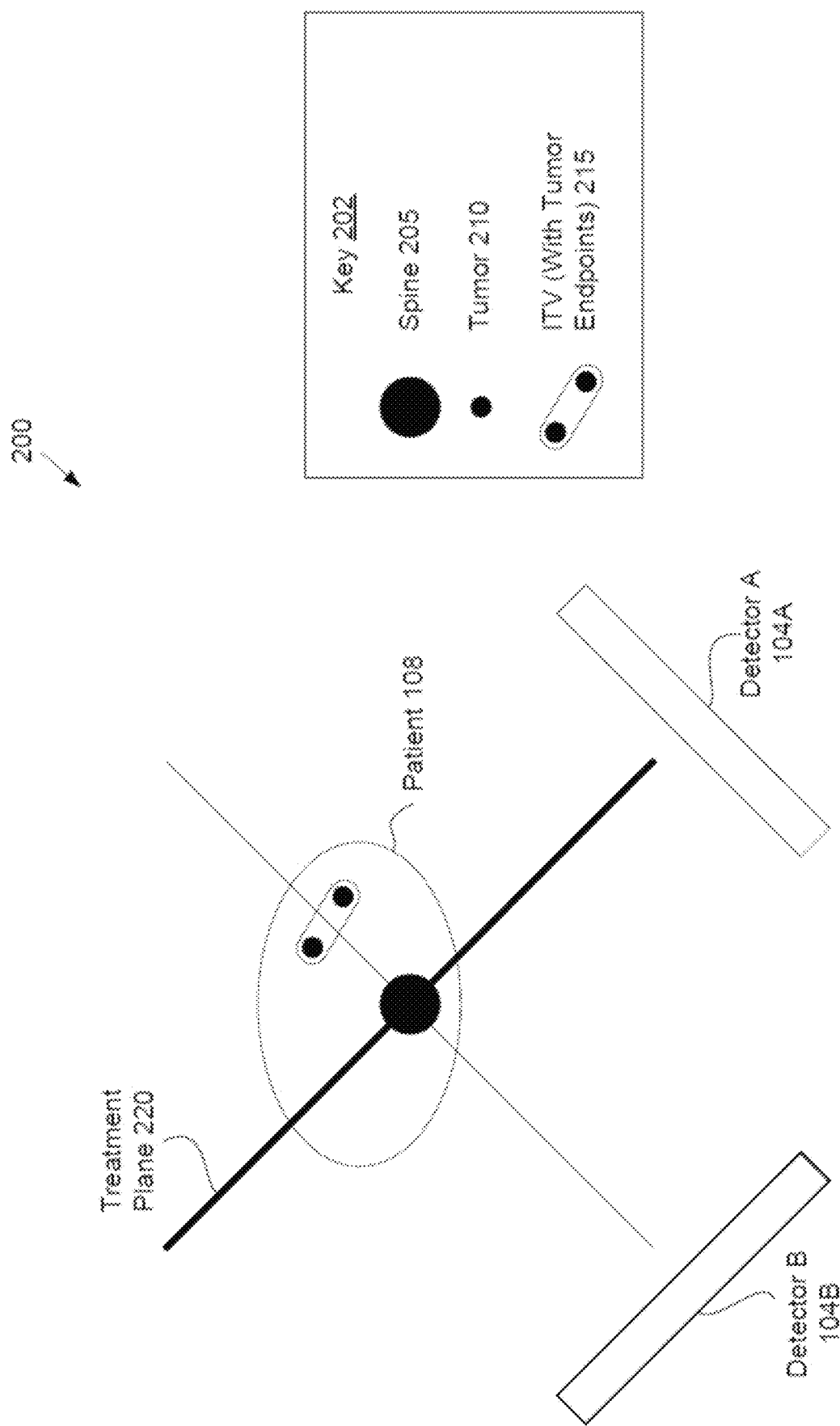
FIG. 2A illustrates a simplified view of the imaging system of FIG. 1B, including internal anatomical structures within a patient, in accordance with embodiments described herein.

FIG. 2A illustrates a simplified view 200 of the imaging system 700 of FIG. 1B, including internal anatomical structures within a patient 108, in accordance with embodiments described herein. FIG. 2A includes a key 202 that identifies a spine 205, a tumor 210 and an ITV 215. In one embodiment, an ITV is the volume defined by the target as it moves through its full range of motion. As shown in this embodiment, the patient's spine 205 is aligned to the treatment center (e.g., the intersection of the imaging axes). This may be performed by positioning the treatment couch 714 that holds the patient 108. The system views the spine 205 in both detectors 104A and 104B. Accordingly, the system aligns the spine 205 in three-dimensional (3D) space by registering stereoscopic x-ray images taken by the detectors 104A, 104B to DRRs generated from an intrafraction image (e.g., a 3D motion image), as will be appreciated by the skilled artisan.

A treatment plane 220 is shown intersecting the spine 205. The treatment plane 220 is a plane that is parallel to the imaging plane of the detector used for tracking (e.g., detector 104B) and that passes through the treatment center. When tracking a target using the 1-view tracking mode, the system determines, from the 1-view available, target VOI locations in the two dimensions of the imaging plane of the detector used for tracking (e.g., detector 104B). The 2D position data may be projected onto the treatment plane to provide a 3D coordinate position from the 2D position data.

In one embodiment, once the system aligns the spine (or other reference, non-target structure) to the treatment center, the system repositions a treatment couch that holds the patient so that the treatment center passes through the center of the ITV 215. In one embodiment, the treatment couch 714 is moved based on a predetermined offset between the spine 205 and a center of the ITV 215, as provided by a treatment plan.

Figure 2B:
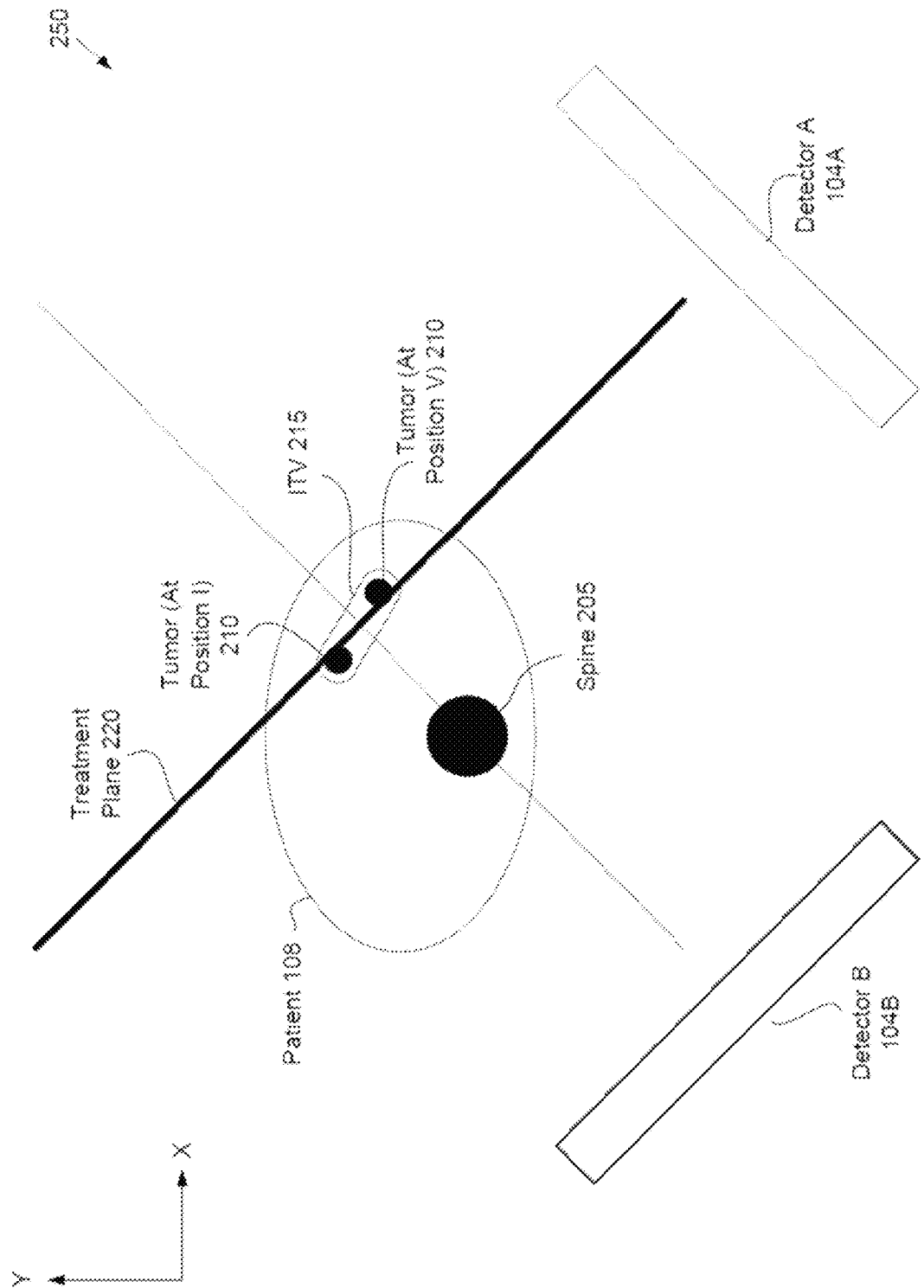
FIG. 2B illustrates a simplified view of the imaging system of FIG. 1B, after a treatment couch has been repositioned so that a treatment center passes through the center of an ITV, in accordance with embodiments described herein.

FIG. 2B illustrates a simplified view of the imaging system 700 of FIG. 1B, after a treatment couch 714 has been repositioned so that a treatment center passes through the center of an ITV 215, in accordance with embodiments described herein. After the treatment couch 714 is moved based on the predetermined offset, a user (e.g., a physician or technician) may adjust a position of the treatment couch 714 to make alignment corrections. In one embodiment, after the initial offset motion, the position of the treatment couch 714 is tightly controlled. In one embodiment, alignment motions out of the treatment plane 220 are not allowed. For example, FIG. 2B shows an x-axis and a y-axis. A user would not be permitted to make an adjustment along just the y-axis or just the x-axis, because this may cause motion outside of the treatment plane 220. Thus, any adjustment in the x-axis may be accompanied by a corresponding adjustment in the y-axis. Similarly, any adjustment in the y-axis may be accompanied by a corresponding adjustment in the x-axis. This ensures that the offset between the spine 206 and the center of the ITV 215 in the axis perpendicular to the treatment plane 220 is not changed.

Figure 3A:
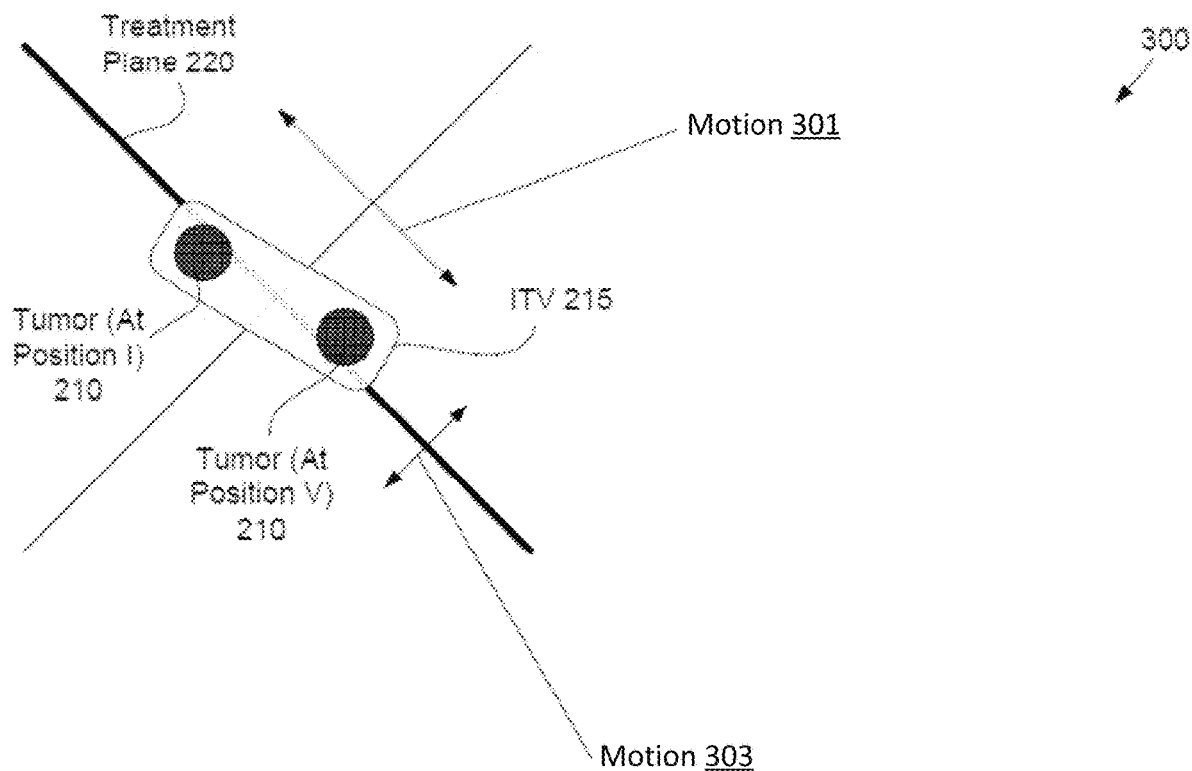
FIG. 3A illustrates a zoomed in view of an ITV, showing motion within a treatment plane, and motion normal to the treatment plane, in accordance with embodiments described herein.

FIG. 3A illustrates a zoomed in view 300 of an ITV 215, showing motion 301 within a treatment plane, and motion 303 normal to the treatment plane, in accordance with embodiments described herein.

In one embodiment, in 1-view tracking mode, motion 301 within a treatment plane 220 is tracked, while motion 303 normal to the treatment plane 220 is not tracked. In another embodiment, in 0-view tracking mode, neither motion 301 within treatment plane 220, nor motion 303 normal to the treatment plane 220 is tracked.

Figure 3B:
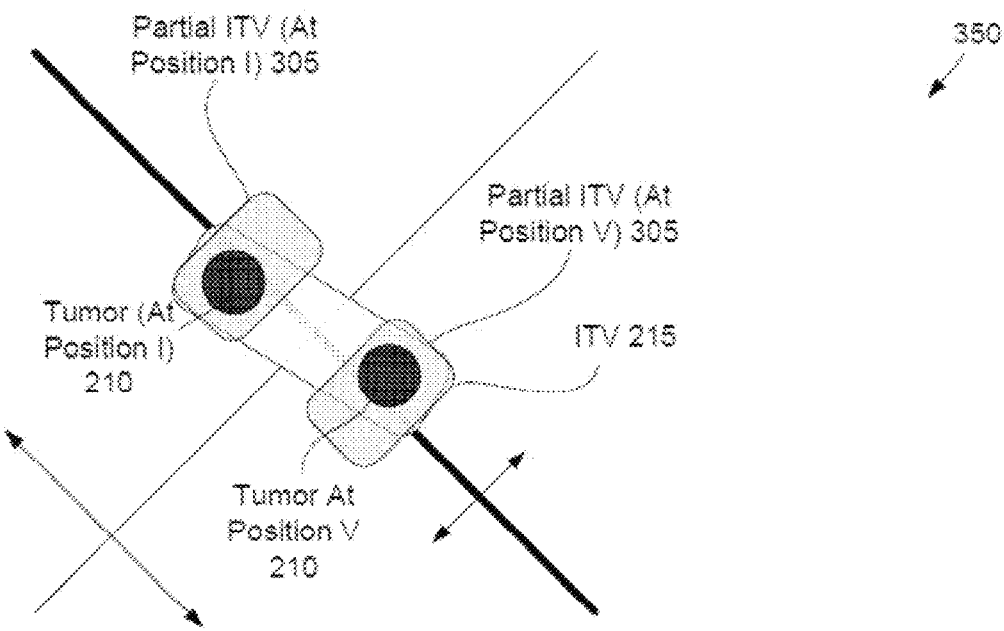
FIG. 3B illustrates another zoomed in view of the ITV, showing a partial-ITV that has been generated by projecting the motion onto the axis normal to the treatment plane, in accordance with embodiments described herein.
Figure 4A:
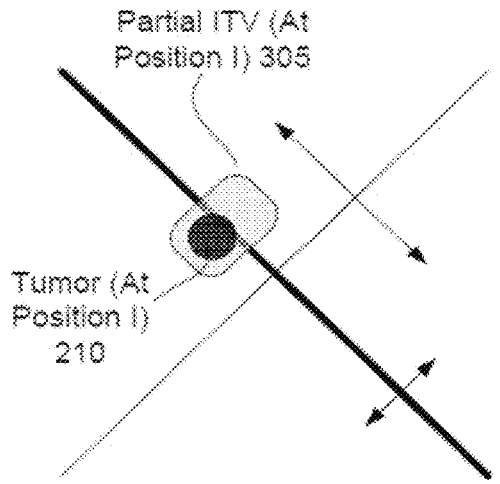
FIGS. 4A-4E show different positions of the tumor during a patient's respiratory cycle, in accordance with embodiments described herein.
Figure 4B:
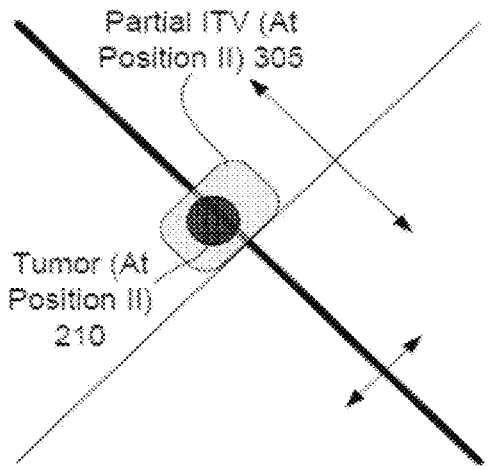
Figure 4C:
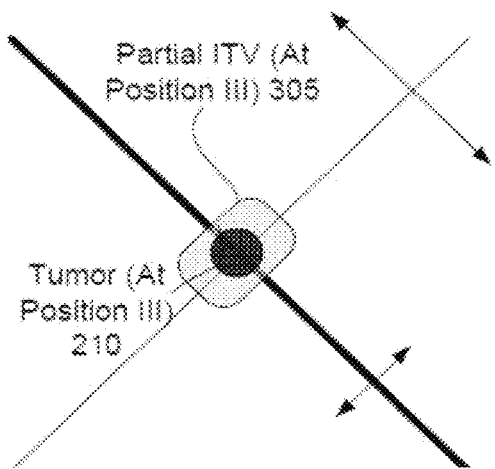
Figure 4D:
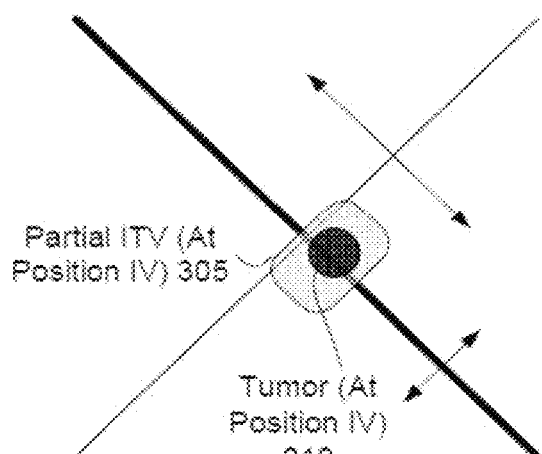
Figure 4E:
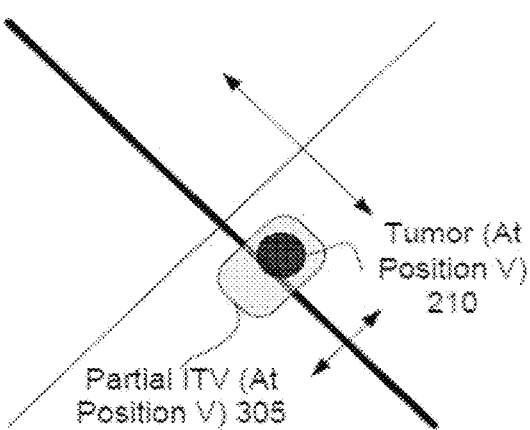

FIG. 3B illustrates another zoomed in view 350 of the ITV 215, showing a partial-ITV 305 that has been generated by projecting the motion (e.g., ITV) onto the axis normal to the treatment plane 220, in accordance with embodiments described herein. This may be performed, for example, by representing the ITV as a three dimensional vector and projecting the three dimensional vector onto the axis normal to the treatment plane. This provides the component of tumor's 210 motion along the axis normal to the treatment plane 220. The tumor 210 and partial ITV 305 are shown at a first position (position I) and at a fifth position (position V). As shown, the partial-ITV 305 is moved inside the treatment plane 220 as the tumor's 210 position changes. However, the partial-ITV 305 is not moved along the axis that is normal to the treatment plane 220.

FIGS. 4A-4E show different positions (e.g., positions I-V) of the tumor 210 during a patient's respiratory cycle, in accordance with embodiments described herein. Tumor movement within the treatment plane 220 can be tracked using detector 104B. Movement outside of, or normal to, the treatment plane may not be tracked because the other detector cannot view the tumor. The system accounts for target VOI motion outside of the treatment plane 220 by treating the partial-ITV 305, and the system tracks and accounts for motion within the treatment plane.

In one embodiment, the system uses a radiation treatment beam to generate diagnostic images. In this embodiment, the system includes a device called an electronic portal imaging device (EPID). The EPID is positioned so as to receive radiation beams generated by a radiation treatment source that have passed through a patient. An EPID uses the radiation treatment beam itself to create portal images that can be used to determine a location of the target VOI. In one embodiment, the EPID includes a two-dimensional area detector, and thus can detect target VOI position within an imaging plane. For such EPIDs, the above described 1-view tracking mode can be used to track target VOI location. For example, the system may generate a partial-ITV by projecting an ITV onto the axis that is normal to the EPIDs imaging plane, as described above.

In one embodiment, the EPID includes a one-dimensional scanning detector. The one-dimensional scanning detector detects target VOI position within an imaging axis. When using an EPID that includes a one-dimensional scanning detector, the system may generate a partial-ITV by projecting the ITV onto the plane to which the imaging axis is normal. Thus, the partial-ITV may account for target VOI motion outside of the imaging axis.

In one embodiment, the system performs a technique called gating (also referred to herein as a gated treatment mode). In the gated treatment mode, the treatment beam is enabled when the estimated target location is within a predefined range, and disabled when the estimated target position is outside this range. The estimation of the target position may take place by direct measurement (for example, by localizing the target in one or more X-ray images), or may take place by a surrogate measurement (for example, by tracking optical markers attached to the exterior of the patient's chest). For a gated treatment mode, the motion range covered by the partial-ITV may span those positions for which the treatment beam will be turned on. For example, the treatment beam may be activated while the tumor is estimated to be within 5 mm of a full exhale tumor position. The partial-ITV may include the motion range of the tumor within those 5 mm. Gating may be used to accommodate cyclic patient motion such as respiratory motion or cardiac motion. In one embodiment, gating is combined with 1-view tracking or with tracking using an EPID. In such an embodiment, the partial-ITV may cover motion of the target VOI in an untracked plane or axis that occurs within a predetermined treatment zone (e.g., during a particular phase of the patient's respiratory cycle). The advantage of using a partial-ITV in conjunction with a gating system, and using the allowed motion range of the gating system to define the partial-ITV, is that the dose distribution displayed at the treatment planning step accurately reflects the amount of tissue that will be exposed to radiation during treatment delivery.

Figure 5A:
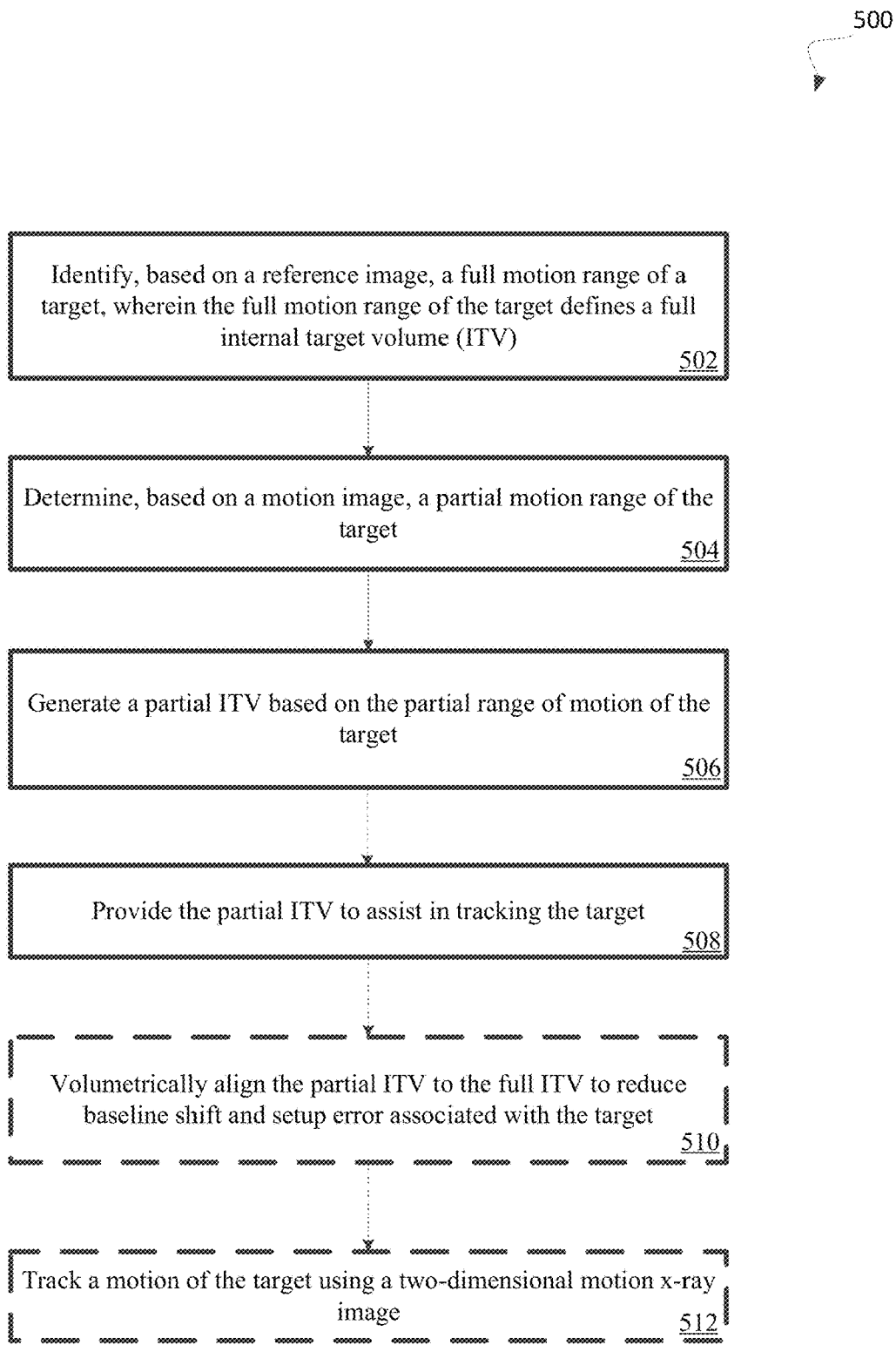
FIG. 5A illustrates a first method of 1-view interfraction treatment target motion management using volumetric imaging, in accordance with embodiments described herein.

FIG. 5A illustrates a first method 500 of 1-view interfraction treatment target motion management using volumetric imaging, in accordance with embodiments described herein. In general, the method 500 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 500 may be performed by processing logic of the radiation treatment system 1200 of FIG. 1. In one embodiment, the operations of method 500 may apply to 1-view tracking.

As shown in FIG. 5, the method 500 may begin with the processing logic identifying, based on a reference image (e.g., a 3D planning image), a full motion range of a target (502). In one embodiment, the reference image is the result of a 3D scan acquired at the beginning of a treatment fraction (e.g., session) to perform direct target alignment. The reference image may be a four-dimensional (4D) planning image. The 4D planning image may be one of: a kilovoltage computed tomography (kV-CT) image, a magnetic resonance imaging (MRI) image, a kilovoltage cone beam computed tomography (kV-CBCT) image, a megavoltage computed tomography (MVCT) image, or any other 4D image. In another embodiment, the reference image is a three-dimensional (3D) inhale and exhale planning image. The 3D inhale and exhale planning image may be one of: a kilovoltage computed tomography (kV-CT) image, a magnetic resonance imaging (MRI) image, a kilovoltage cone beam computed tomography (kV-CBCT) image, a megavoltage computed tomography (MVCT) image, or any other 3D image. This step may remove an interfraction baseline shift. In one embodiment, the full motion range of the target defines a full ITV.

Processing logic may, at block 504, determine, based on a motion image (e.g., a 3D intrafraction image), a partial motion range of the target. In one embodiment, the motion image is a three-dimensional (3D) intrafraction image. The 3D intrafraction image may be one of: a kilovoltage cone beam computed tomography (kV-CBCT) image, a megavoltage cone beam computed tomography (MV-CBCT) image, a megavoltage computed tomography (MVCT) image, or any other 3D image. In one embodiment, the reference image and the motion image may be generated by an imaging source of a helical radiation delivery system or by one or more imaging sources at different positions with respect to a patient, as described herein.

In one embodiment, the partial motion range is an untracked portion of the full motion range of the target. The partial motion range may include one of an untracked plane or an untracked axis. At block 506, processing logic may generate, by a processing device, a partial ITV based on the partial range of motion of the target. In one embodiment, the partial ITV is a volume swept by the target as the target moves through the partial motion range. In one embodiment, the partial ITV is smaller than the full ITV.

At block 508, processing logic may provide the partial ITV to assist in tracking the target. Specifically, subsequent target motion (e.g., respiratory motion) may be managed via 1-view tracking, in which the target motion within a plane coincident with the patient inf-sup axis is tracked directly. The partial ITV may be used to compensate for the untracked plane or axis.

In one embodiment, processing logic may volumetrically align the partial ITV to the full ITV to reduce baseline shift and setup error associated with the target (block 510). In another embodiment, processing logic may track a motion of the target using a two-dimensional motion x-ray image.

Figure 5B:
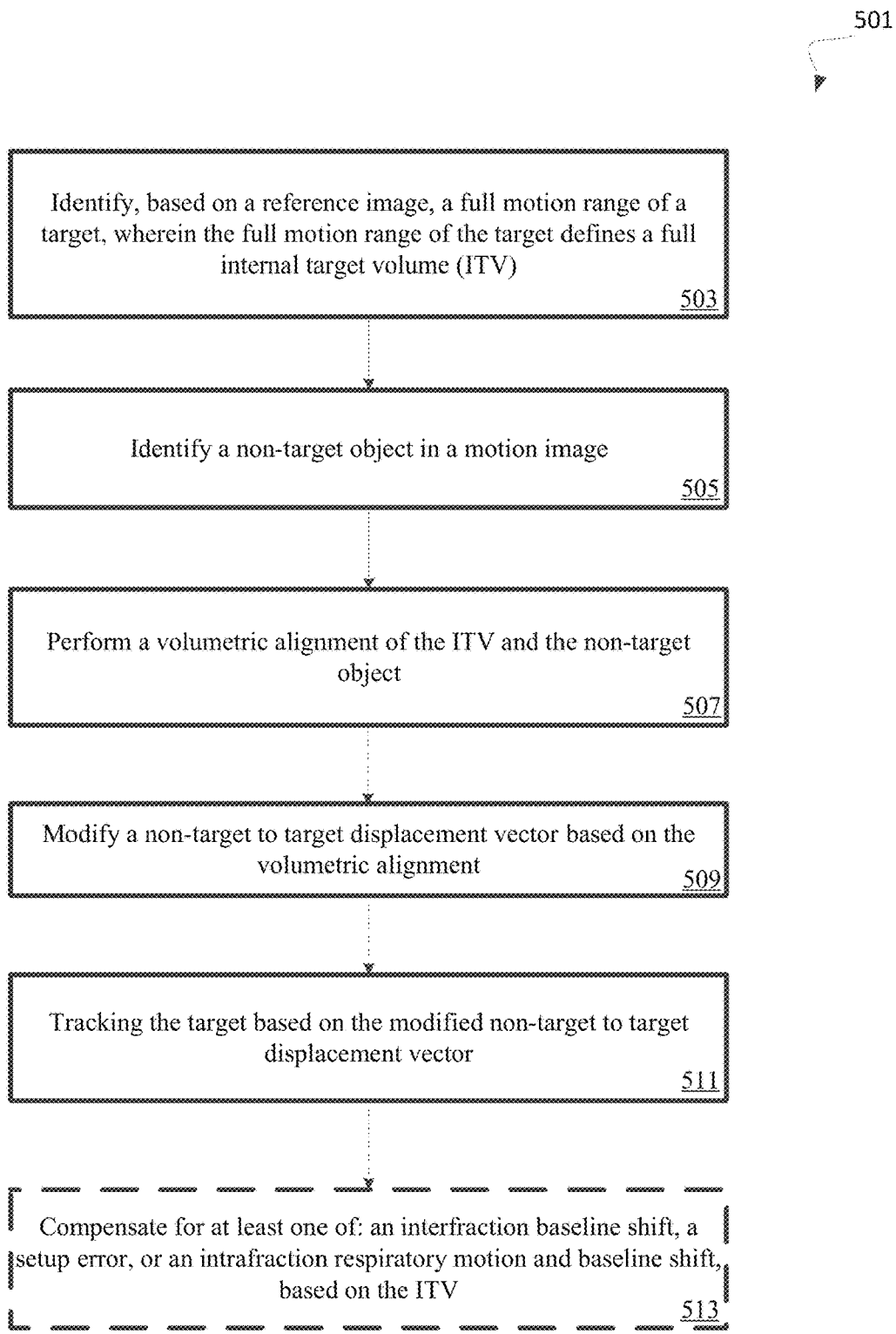
FIG. 5B illustrates a second method of 1-view interfraction treatment target motion management using volumetric imaging, in accordance with embodiments described herein.

FIG. 5B illustrates a second method 501 of 1-view interfraction treatment target motion management using volumetric imaging, in accordance with embodiments described herein. In general, the method 501 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 501 may be performed by processing logic of the radiation treatment system 1200 of FIG. 1. In one embodiment, the operations of method 501 may apply to 0-view tracking.

At block 503, processing logic begins by identifying, based on a reference image, a full motion range of a target. In one embodiment, the full motion range of the target defines a full ITV. As described herein, the reference image may be the result of a 3D scan acquired at the beginning of a treatment fraction (e.g., session) to perform direct target alignment. The reference image may be a four-dimensional (4D) planning image. The 4D planning image may be one of: a kilovoltage computed tomography (kV-CT) image, a magnetic resonance imaging (MRI) image, a kilovoltage cone beam computed tomography (kV-CBCT) image, a megavoltage computed tomography (MVCT) image, or any other 4D image. In another embodiment, the reference image is a three-dimensional (3D) inhale and exhale planning image. The 3D inhale and exhale planning image may be one of: a kilovoltage computed tomography (kV-CT) image, a magnetic resonance imaging (MRI) image, a kilovoltage cone beam computed tomography (kV-CBCT) image, a megavoltage computed tomography (MVCT) image, or any other 3D image. This step may remove an interfraction baseline shift.

At block 505, processing logic identifies a non-target object in a motion image and/or in the reference image. As described herein, a non-target object may include a bony structure, soft tissue, or fiducials, or any other object not being directly tracked. In one embodiment, the non-target object is the spine of a patient. The motion image may be a three-dimensional (3D) intrafraction image, including: a kilovoltage cone beam computed tomography (kV-CBCT) image, a megavoltage cone beam computed tomography (MV-CBCT) image, a megavoltage computed tomography (MVCT) image, or any other 3D image.

At block 507, processing logic performs a volumetric alignment of the ITV and the non-target object. In one embodiment, the volumetric alignment may reduce baseline shift and setup error associated with the target. In one embodiment, performing the volumetric alignment of the ITV and the non-target object includes performing two independent rigid registrations using determined registration regions of interest (ROI), or by deformable registration.

At block 509, processing logic modifies, by a processing device, a non-target to target displacement vector based on the volumetric alignment. The non-target displacement vector may be between a reference point on the non-target object and the center of the target as defined by the reference image.

At block 511, processing logic tracks, by the processing device, the target based on the modified non-target to target displacement vector. During treatment, the same non-target displacement vector may be applied after each non-target object tracking correction in order to estimate the position of the target. At block 513, processing logic may compensate for at least one of: an interfraction baseline shift, a setup error, a change in patient anatomy, or an intrafraction respiratory motion and baseline shift, based on the ITV. In one embodiment, a change in patient anatomy may include a change in objects (e.g., non-target organs or other objects) less than a defined proximity threshold to the target. It should be repeated that in one embodiment, the reference image and the motion image may be generated by an imaging source of a helical radiation delivery system or by one or more imaging sources at different positions with respect to a patient, as described herein.

It should be noted that the embodiments described herein can be used with various types of planning image types, including diagnostic kV-CT, MRI, kV-CBCT, and MVCT. The methods discussed herein may be used with MR-based planning (e.g., in the case where no CT is used or available for treatment planning). The embodiments discussed herein can also be used with various types of intrafraction 3D images, including kV-CBCT, MVCT, MVCBCT, and in-room helical/diagnostic kV-CT. The embodiments discussed herein can be used with various types of intrafraction 2D imaging systems, including stereo x-ray pair, a rotating monoscopic 2D x-ray imager, and C-arm intraoperative imaging systems (used in surgical and interventional guidance applications). Although the embodiments are described at times in relation to a robotic surgery system, in alternative embodiments, the method discussed herein may be used with other types of treatment delivery systems such as a helical delivery system and gantry-based systems. In addition, although the embodiments are described at times in relation to the medPhoton ImagingRing System (IRS), in alternative embodiments, the methods may be used with other types of volumetric imaging systems.

Figure 6:
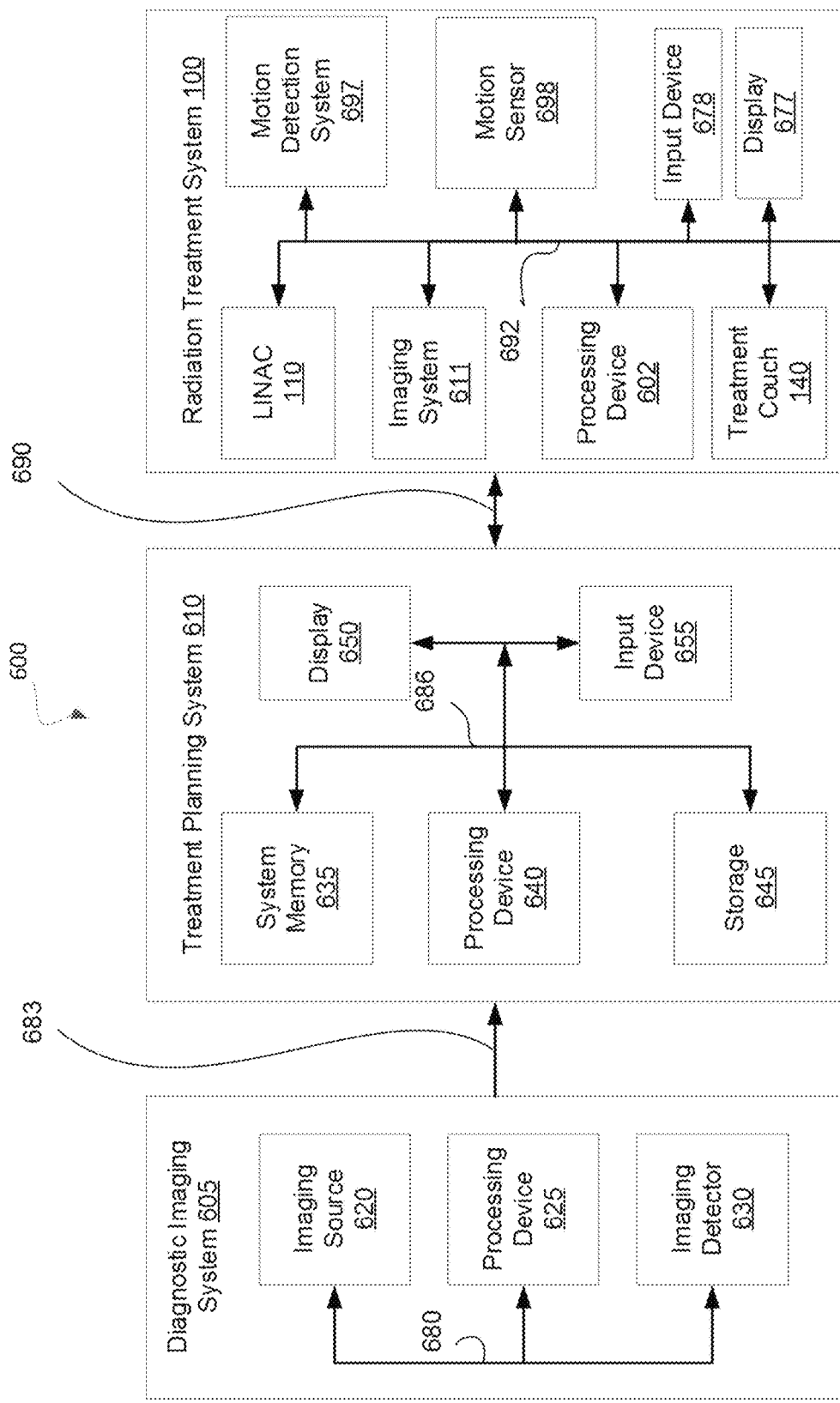
FIG. 6 illustrates a system that may be used in the generating of the performing of radiation treatment, in accordance with embodiments described herein.

FIG. 6 illustrates an example machine of a computer system 600 within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 600 includes a processing device 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 618, which communicate with each other via a bus 630.

Processing device 602 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute instructions 626 for performing the operations and steps discussed herein.

The computer system 600 may further include a network interface device 608 to communicate over the network 620. The computer system 600 also may include a video display unit 610 (e.g., a liquid crystal display (LCD) or a cathode ray tube (CRT)), an alphanumeric input device 612 (e.g., a keyboard), a cursor control device 614 (e.g., a mouse), a graphics processing unit 622, a signal generation device 616 (e.g., a speaker), graphics processing unit 622, video processing unit 628, and audio processing unit 632.

The data storage device 618 may include a machine-readable storage medium 624 (also known as a computer-readable medium) on which is stored one or more sets of instructions or software 626 embodying any one or more of the methodologies or functions described herein. The instructions 626 may also reside, completely or at least partially, within the main memory 604 and/or within the processing device 602 during execution thereof by the computer system 600, the main memory 604 and the processing device 602 also constituting machine-readable storage media.

In one implementation, the instructions 626 include an x-ray motion component 699 to implement functionality corresponding to the disclosure herein. While the machine-readable storage medium 624 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Figure 7:
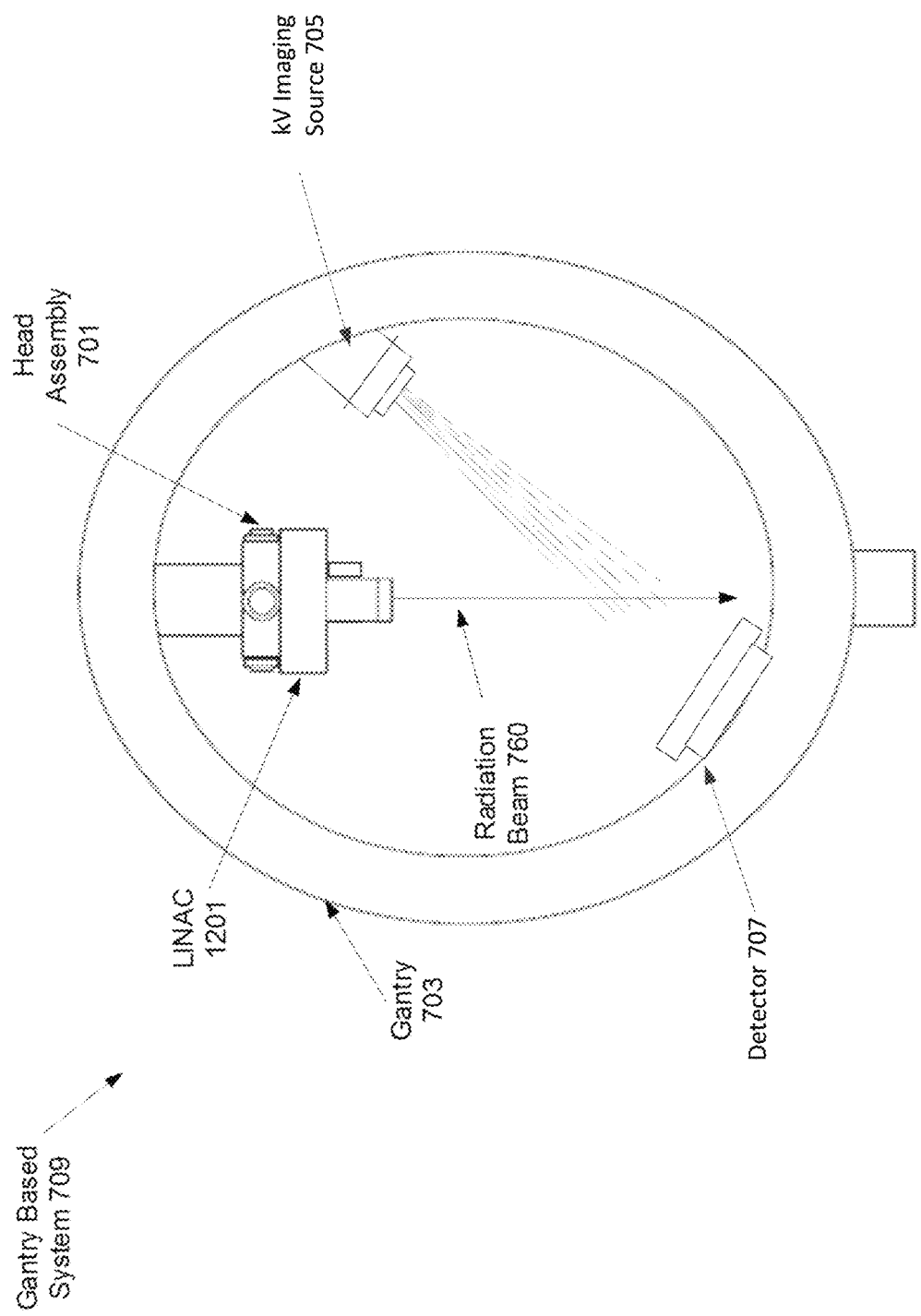
FIG. 7 illustrates a gantry based intensity modulated radiotherapy system, in accordance with embodiments described herein.

FIG. 7 illustrates a gantry based intensity modulated radiotherapy (IMRT) system 709, in accordance with implementations of the present disclosure. In gantry based system 709, a radiation source (e.g., a LINAC 1201) having a head assembly 701 is mounted on a gantry 703. In one embodiment, radiation beams 160 may be delivered from several positions on a circular plane of rotation (e.g., around an axis of rotation). In one embodiment, system 709 includes a treatment imaging system, which may include a kV imaging source 705 and an x-ray detector 707. The kV imaging source 705 may be used to generate x-ray images of a ROI of patient by directing a sequence of x-ray beams at the ROI which are incident on the x-ray detector 707 opposite the kV imaging source 705 to image the patient for setup and generate in-treatment images. The resulting system generates arbitrarily shaped radiation beams 760 that intersect each other at an isocenter to deliver a dose distribution to the target location. In one implementation, the gantry based system 700 may be a c-arm based system.

Figure 8:
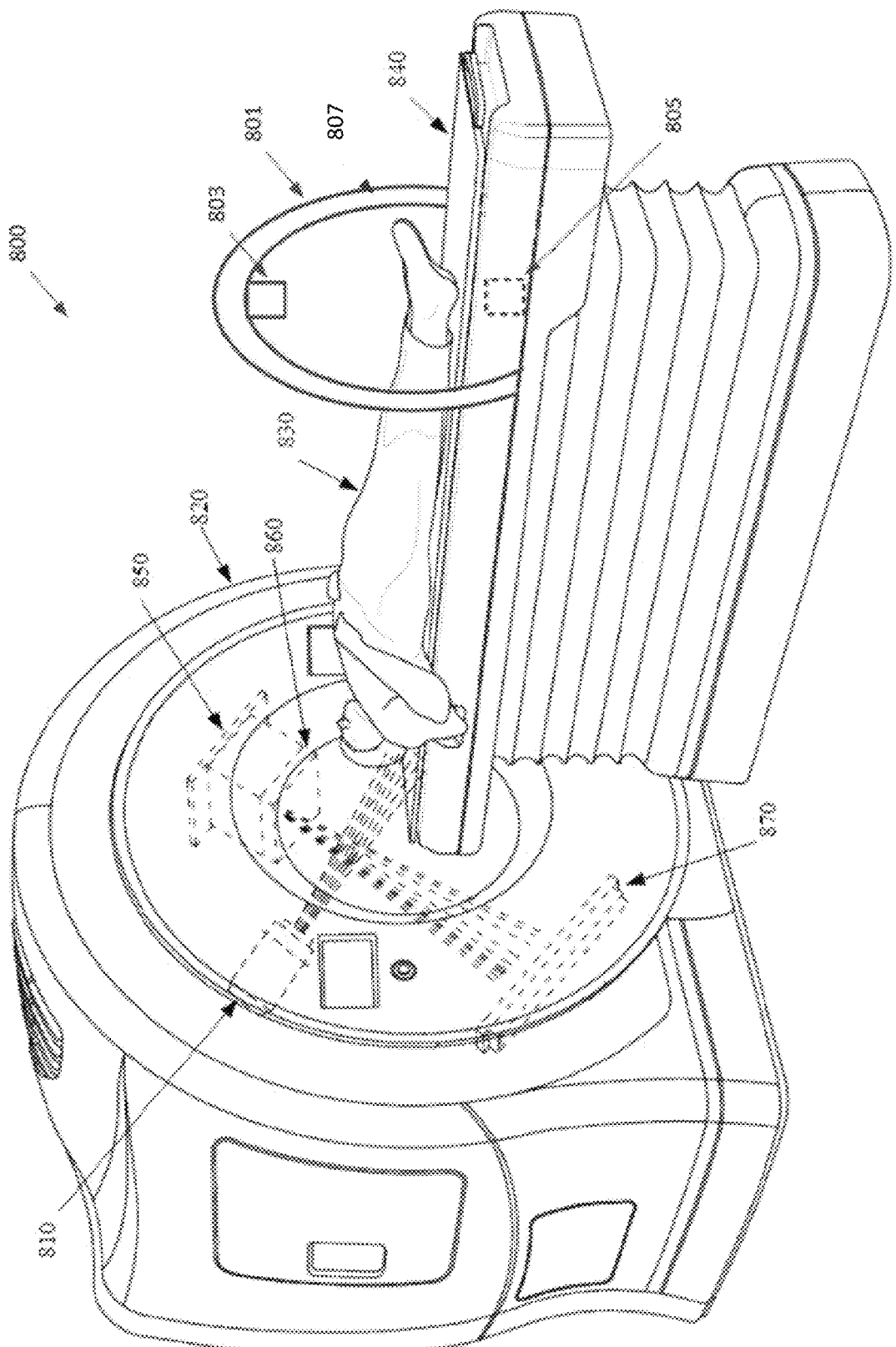
FIG. 8 illustrates a helical radiation delivery system, in accordance with embodiments described herein.

FIG. 8 illustrates a helical radiation delivery system 800 in accordance with embodiments of the present disclosure. The helical radiation delivery system 800 may include a linear accelerator (LINAC) 810 mounted to a ring gantry 820. The LINAC 810 may be used to generate a narrow intensity modulated pencil beam (i.e., treatment beam) by directing an electron beam towards an x-ray emitting target. The treatment beam may deliver radiation to a target region (i.e., a tumor). The ring gantry 820 generally has a toroidal shape in which the patient 830 extends through a bore of the ring/toroid and the LINAC 810 is mounted on the perimeter of the ring and rotates about the axis passing through the center to irradiate a target region with beams delivered from one or more angles around the patient. During treatment, the patient 830 may be simultaneously moved through the bore of the gantry on treatment couch 840.

The helical radiation delivery system 800 includes a treatment imaging system, which may include a kV imaging source 850 and an x-ray detector 870. The kV imaging source 850 may be used to generate x-ray images of a region of interest (ROI) of patient 830 by directing a sequence of x-ray beams at the ROI which are incident on the x-ray detector 870 opposite the kV imaging source 850 to image the patient 830 for setup and generate in-treatment images. The treatment imaging system may further include a collimator 860. In one embodiment, the collimator 860 may be a variable aperture collimator. In another embodiment, the collimator 860 may be a multi-leaf collimator (MLC). The MLC includes a housing that houses multiple leaves that are movable to adjust an aperture of the MLC to enable shaping of an imaging x-ray beam. In another embodiment, the variable aperture collimator 860 may be an iris collimator containing trapezoidal blocks that move along a frame in a manner similar to a camera iris to produce an aperture of variable size that enables shaping of the imaging x-ray beam. The kV imaging source 850 and the x-ray detector 870 may be mounted orthogonally relative to the LINAC 810 (e.g., separated by 90 degrees) on the ring gantry 820 and may be aligned to project an imaging x-ray beam at a target region and to illuminate an imaging plane of detector 870 after passing through the patient 130. In some embodiments, the LINAC 810 and/or the kV imaging source 850 may be mounted to a C-arm gantry in a cantilever-like manner, which rotates the LINAC 810 and kV imaging source 850 about the axis passing through the isocenter. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Helical radiation delivery system 800 includes also includes a secondary imaging system 801. Imaging system 801 is a CBCT imaging system, for example, the medPhoton ImagingRing System. Alternatively, other types of volumetric imaging systems may be used. The secondary imaging system 801 includes a rotatable gantry 807 (e.g., a ring) attached to anarm and rail system (not shown) that move the rotatable gantry 807 along one or more axes (e.g., along an axis that extends from a head to a foot of the treatment couch 840. An imaging source 803 and a detector 805 are mounted to the rotatable gantry 807. The rotatable gantry 807 may rotate 360 degrees about the axis that extends from the head to the foot of the treatment couch. Accordingly, the imaging source 803 and detector 805 may be positioned at numerous different angles. In one embodiment, the imaging source 803 is an x-ray source and the detector 805 is an x-ray detector. In one embodiment, the secondary imaging system 801 includes two rings that are separately rotatable. The imaging source 803 may be mounted to a first ring and the detector 805 may be mounted to a second ring.

It will be apparent from the foregoing description that aspects of the present disclosure may be embodied, at least in part, in software. That is, the techniques may be carried out in a computer system or other data processing system in response to a processing device 625, 640, or 602 (see FIG. 6), for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 625, 640, or 602.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing at least one of software programs or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method, comprising:
    identifying, based on a reference image, a full motion range of a target, wherein the full motion range of the target defines a full internal target volume (ITV), wherein the reference image is a four-dimensional (4D) inhale and exhale planning image;
    identifying a non-target object in a motion image or the reference image;
    determining, based on a volumetric alignment of the ITV and the non-target object, a non-target to target displacement vector between a reference point on the non-target object and a center of the target as defined by the reference image based on the volumetric alignment, wherein the non-target to target displacement vector defines an estimated relative position of the target with respect to the non-target object; and
    applying, by a processing device, the same non-target to target displacement vector at the reference point on the non-target object after each of a plurality of non-target object corrections to perform 0-view tracking of the target indirectly based on the non-target to target displacement vector without tracking the target directly in the motion image, wherein the target displacement vector is to compensate for gross motion of the target within a treatment fraction; and
    compensating for baseline shift between treatment fractions based on the ITV.

2. The method of claim 1, further comprising compensating for at least one of:, a setup error, a change in patient anatomy, or an intrafraction respiratory motion and baseline shift, based on the ITV.

3. The method of claim 1, wherein the 4D inhale and exhale planning image is one of: a kilovoltage computed tomography (kV-CT) image, a magnetic resonance imaging (MRI) image, a kilovoltage cone beam computed tomography (kV-CBCT) image, or a megavoltage computed tomography (MVCT) image.

4. The method of claim 1 further comprising performing the volumetric alignment of the ITV and the non-target object including: performing two independent rigid registrations using determined registration regions of interest (ROI), or by deformable registration.

5. The method of claim 1, wherein the reference image or the motion image are generated by an imaging source of a helical radiation delivery system or by one or more imaging sources at different positions with respect to a patient.

6. A system comprising:
    a memory; and
    a processing device, operatively coupled with the memory, to:
        identify, based on a reference image, a full motion range of a target, wherein the full motion range of the target defines a full internal target volume (ITV), wherein the reference image is a four-dimensional (4D) inhale and exhale planning image;
        identify a non-target object in a motion image or the reference image;

determine, based on a volumetric alignment of the ITV and the non-target object, a non-target to target displacement vector between a reference point on the non-target object and a center of the target defined by the reference image based on the volumetric alignment, wherein the non-target to target displacement vector defines an estimated relative position of the target with respect to the non-target object;

apply the same non-target to target displacement vector at the reference point on the non-target object after each of a plurality of non-target object corrections to perform 0-view tracking of the target indirectly based on the non-target to target displacement vector without tracking the target directly in the motion image, wherein the target displacement vector is to compensate for gross motion of the target within a treatment fraction; and compensate for baseline shift between treatment fractions based on the ITV.

7. The system of claim 6, wherein the processing device is further to compensate for at least one of: a setup error, a change in patient anatomy, or an intrafraction respiratory motion and baseline shift, based on the ITV.

8. The system of claim 6, wherein the 4D inhale and exhale planning image is one of: a kilovoltage computed tomography (kV-CT) image, a magnetic resonance imaging (MRI) image, a kilovoltage cone beam computed tomography (kV-CBCT) image, or a megavoltage computed tomography (MVCT) image.

9. The system of claim 6, wherein the processing device is further to perform the volumetric alignment of the ITV and the non-target object including to: perform two independent rigid registrations using determined registration regions of interest (ROI), or by deformable registration.

10. The system of claim 6, wherein the reference image or the motion image are generated by an imaging source of a helical radiation delivery system or by one or more imaging sources at different positions with respect to a patient.

11. A non-transitory computer readable medium comprising instructions that, when executed by a processing device, cause the processing device to:

identify, based on a reference image, a full motion range of a target, wherein the full motion range of the target defines a full internal target volume (ITV);

identify a non-target object in a motion image or the reference image, wherein the motion image is a four-dimensional (4D) inhale and exhale intrafraction image;

determine, based on a volumetric alignment of the ITV and the non-target object, a non-target to target displacement vector between a reference point on the non-target object and a center of the target as defined by the reference image based on the volumetric alignment, wherein the non-target to target displacement vector defines an estimated relative position of the target with respect to the non-target object;

apply, by the processing device, the same non-target to target displacement vector at the reference point on the non-target object after each of a plurality of non-target object corrections to perform 0-view tracking of the target indirectly based on the non-target to target displacement vector without tracking the target directly in the motion image, wherein the target displacement vector is to compensate for gross motion of the target within a treatment fraction; and compensate for baseline shift between treatment fractions based on the ITV.

12. The non-transitory computer readable medium of claim 11, wherein the processing device is further to compensate for at least one of: a setup error, a change in patient anatomy, or an intrafraction respiratory motion and baseline shift, based on the ITV.

13. The non-transitory computer readable medium of claim 11, wherein the reference image is a four-dimensional (4D) or a three-dimensional (3D) inhale and exhale planning image, and wherein the 4D inhale and exhale planning image is one of: a kilovoltage computed tomography (kV-CT) image, a magnetic resonance imaging (MRI) image, a kilovoltage cone beam computed tomography (kV-CBCT) image, or a megavoltage computed tomography (MVCT) image.

14. The non-transitory computer readable medium of claim 11, wherein the reference image is a three-dimensional (3D) planning image, and wherein the 3D planning image is one of: a kilovoltage computed tomography (kV-CT) image, a magnetic resonance imaging (MRI) image, a kilovoltage cone beam computed tomography (kV-CBCT) image, or a megavoltage computed tomography (MVCT) image.

15. The non-transitory computer readable medium of claim 11, wherein the processing device is further to perform the volumetric alignment of the ITV and the non-target object including to: perform two independent rigid registrations using determined registration regions of interest (ROI), or by deformable registration.

16. The non-transitory computer readable medium of claim 11, wherein the non-target is a spine of a patient and wherein to track the target based on the modified non-target to target displacement vector, the processing device is to track gross patient motion with respect to the spine.

* * * * *